United States Patent [19]

Visveshwara et al.

[11] Patent Number: 5,443,060
[45] Date of Patent: Aug. 22, 1995

[54] SYSTEM FOR SUPPORTING ENDOTRACHEAL TUBES IN PEDIATRIC PATIENTS AND METHOD OF USING SAME

[75] Inventors: Nadarasa Visveshwara; Roy Oto, both of Fresno, Calif.

[73] Assignee: Novametrix Medical Systems, Inc., Wallingford, Conn.

[21] Appl. No.: 177,535

[22] Filed: Jan. 5, 1994

[51] Int. Cl.6 ............................................. A61M 16/00
[52] U.S. Cl. .................... 128/200.26; 128/207.14; 128/DIG. 26
[58] Field of Search ................ 128/200.26, 207.14, 128/207.15, 912, DIG. 26

[56] References Cited

U.S. PATENT DOCUMENTS

| | | | |
|---|---|---|---|
| 900,343 | 10/1908 | Barnes | 128/207.14 |
| 2,693,182 | 11/1954 | Phillips | 128/207.14 |
| 2,908,269 | 10/1959 | Cheng | 128/DIG. 26 |
| 3,774,616 | 11/1973 | White et al. | 128/DIG. 26 |
| 3,927,676 | 12/1975 | Schulz . | |
| 4,112,936 | 9/1978 | Blachly . | |
| 4,167,946 | 9/1979 | Sandstrom . | |
| 4,191,180 | 3/1980 | Colley et al. | 128/207.17 |
| 4,223,671 | 9/1980 | Muto | 128/200.26 |
| 4,249,529 | 2/1981 | Nestor et al. | 128/207.17 |
| 4,270,529 | 6/1981 | Muto | 128/200.26 |
| 4,270,531 | 6/1981 | Blachly et al. | 128/207.14 |
| 4,313,437 | 2/1982 | Martin | 128/207.17 |
| 4,351,331 | 9/1982 | Gereg | 128/DIG. 26 |
| 4,367,735 | 1/1983 | Dali | 128/207.18 |
| 4,475,548 | 10/1984 | Muto | 128/912 |
| 4,480,639 | 11/1984 | Peterson et al. | 128/207.18 |
| 4,548,200 | 10/1985 | Wapner | 128/207.17 |
| 4,774,946 | 11/1988 | Ackerman et al. | 128/207.18 |
| 4,791,914 | 12/1988 | May | 128/10 |
| 4,838,255 | 6/1989 | Lambert | 128/202.16 |
| 4,906,234 | 3/1990 | Voychehovski | 604/79 |
| 4,919,126 | 4/1990 | Baildon | 128/207.14 |
| 5,009,227 | 4/1991 | Nieuwstad | 128/207.17 |
| 5,069,206 | 12/1991 | Crosbie | 128/207.17 |
| 5,174,283 | 12/1992 | Parker | 128/207.14 |
| 5,181,505 | 1/1993 | Lew et al. | 128/207.15 |
| 5,195,513 | 3/1993 | Sinko et al. | 128/207.14 |
| 5,305,742 | 4/1994 | Styers et al. | 128/DIG. 26 |

OTHER PUBLICATIONS

Erenberg, et al., "Palatal Groove Formation in Neonates and Infants With Orotracheal Tubes", Department of Pediatrics, University of Iowa Hospitals and Clinics, Iowa City, ADJC, vol. 138, pp. 974–975, Oct. 1984.

(List continued on next page.)

Primary Examiner—Edgar S. Burr
Assistant Examiner—Aaron J. Lewis
Attorney, Agent, or Firm—Hopgood, Calimafde, Kalil & Judlowe

[57] ABSTRACT

A system and method are disclosed for supporting orotracheal tubing in the mouth and trachea of pediatric patient (e.g., infant) during prolonged intubation. In general, the system comprises an intraoral component and an extraoral component, each of unitary construction. The intraoral components includes a base portion and an alveolar ridge cushioning flap portion. The base portion has a longitudinal extent, a bore formed along the longitudinal extent for passage and support of a first selected portion of the endotracheal tubing, and a palate facing surface made of a soft resilient material for cushioning the palate of the infant during intubation. The extraoral component of the system includes a flexible lip cushioning flap portion and a tubing clasping portion. A centrally disposed hole is formed in the lip cushioning flap portion for releasable receipt of a projection extending from the alveolar ridge cushioning portion. A substantially rigid stem portion extends from the central portion of the lip cushioning flap portion. A tubing clasping portion extends from the substantially rigid stem portion, and is adapted to releasably clasp a second selected portion of the endotracheal tubing. Advantageously, the system and method of the present invention avoids the need to custom fit the intraoral component to the surface contour to each infant's palate, nor requires a snug fit between the palate cushioning structure and the infant's palate, thus reducing the risk of infection.

18 Claims, 3 Drawing Sheets

OTHER PUBLICATIONS

Erenberg, et al., "Appliance for stabilizing orogastric and orotracheal tubes in infants", Department of Pediatrics, University of Iowa Hospitals and Clinics, and Department of Pedodontics, University of Iowa College of Dentistry, vol. 12, No. 8, pp. 669-671, Aug. 1984.

Fadavai, et al., "An Intraoral Prosthetic Appliance for the Prevention of Palatal Grooving in Premature Intubated Infants", Clinical Preventive Dentistry, vol. 12, No. 1, pp. 9-12, Apr.-May 1990.

Sullivan, "An Appliance to Support Oral Intubation in the Premature Infant", Department of Child Dental Health, The London Hospital Medical College, pp. 191-194, 1982.

Ginoza, et al., "Prevention of Palatal Groove Formation with Prolonged Orotracheal Intubation in Preterm Infants", Clinical Research, Division of Neonatal Perinatal Medicine, Miller Children's Hospital, University of California, Irvine, 1989.

Saunders, et al., "Acquired Palatal Groove In Neonates", The Journal of Pediatrics, Dept. of Pediatrics, University of California, San Diego & Dept. of Laboratory Medicine, Sunrise Hospital, vol. 89, No. 6, pp. 988-989, Dec. 1976.

Molteni, et al., "Development and Severity of Palatial Grooves in Orally Intubated Newborns"; Effect of 'Soft' Endotracheal Tubes, Div. of Neonatology, Dept. of Pediatrics, The Johns Hopkins Hosp., Baltimore, AJDC, vol. 140, pp. 357-359; Apr. 1986.

Duke, et al., "Cleft palate associated with prolonged orotracheal intubation in infancy", The Journal of Pediatrics, Department of Pediatrics, Stanford University School of Medicine, vol. 89, No. 6, pp. 990-991, Dec. 1976.

Fadavi, et al., "The oral effects of orotracheal intubation in prematurely born preschoolers", Department of Pediatric Dentistry, University of Illinois at Chicago, Journal of Dentistry for Children, pp. 420-424, Nov.--Dec. 1992.

Fadavi, et al., "Use of a palatal stabilizing device in prevention of palatal grooves in premature infants", Division of Neonatology and the Department of Pediatric Dentistry, University of Illinois at Chicago, vol. 18, No. 11, pp. 1279-1281, Nov. 1990.

Rotschild, et al., "Midfacial Hypoplasia Associated With Long-term Intubation for Bronchopulmonary Dysplasia", Department of Pediatrics, AJDC, vol. 144, pp. 1302-1306, Dec. 1990.

000
SYSTEM FOR SUPPORTING ENDOTRACHEAL TUBES IN PEDIATRIC PATIENTS AND METHOD OF USING SAME

BACKGROUND OF INVENTION

1. Field of Invention

The present invention generally relates to an improved system and method for supporting endotracheal and like medical tubing in pediatric patients, and more particularly a system and method of achieving the same without causing palatal groove formation, acquired cleft palate, defective primary dentition or oral infection during prolonged intubation.

2. Brief Description of the Prior Art

Typically, infants suffering from respiratory failure require mechanically-assisted ventilation. In general, the delivery of gases to the lungs of such infants is achieved through an endotracheal tube. According to convention, one end of the endotracheal tube extends through the mouth and trachea of the infant, while the other end is connected to a mechanical ventilator. Often, artificial ventilation of such infants is conducted for days and sometimes weeks and months until the premature infant's respiratory capacity is sufficiently developed to be safely removed from the artificial ventilator. During the entire intubation period, the endotracheal tube is retained within the trachea and oral cavity of the infant.

It has been known for some time that prolonged intubation using the endotracheal tube can cause a palatal groove which, by definition, is an architectural deformity of the palate caused by constant external pressure on the palatal surface by the endotracheal tube. Studies have shown that the incidence of palatal groove formation increases with the increasing duration of intubation. Studies have also shown that infants who have been intubated for prolonged time periods, typically exhibit poor speech intelligibility, cross bite formation, and high dental vaults later in childhood, and speculate that the palatal groove itself may have an effect on poor phonation and disturbed dental positioning.

Studies also indicate that prolonged intubation may cause complications to the maxillary alveolar ridge, development of a cleft palate, and defective primary dentition due to the constant pressure of the tube in the oral cavity, and tracheal mucosal damage.

Hitherto, a number of prior art intraoral appliances and methods of making and using the same have been developed in order to stabilize endotracheal tubes on the palate, while attempting to prevent the formation of palatal groove and decrease damage to the airway mucosa and vocal cords, and the potential for accidental extubation and defective dentition. Such prior art activity is described in the following publications: "An Intraoral Appliance to Stabilize Orogastric Tubes in Premature Infants, by P. G. Sullivan published in Volume 1 of Lancet, pages 416–147, 1981; "An Appliance to Support oral Intubation in the Premature Infant: by P. G. Sullivan published in Volume 152, Number 6 of the British Dental Journal, pages 191–194, Mar. 16, 1982; An intraoral Prosthetic Appliance for the Prevention of Palatal Grooving in Premature Intubated Infants," by Shahrbanoo Fadavi, et al., published in Volume 12, No. 1, Clinical Preventative Dentistry, at pages 9–12, April-May 1990; "Use of a Palatal Stabilizing Device in the Prevention of Palatal Grooves in Premature Infants" by Shahrbanoo Fadavi, et al., published in Volume 18, No. 11, of Critical Care Medicine, at pages 1279–1281, November, 1990; and United States Letters Patent No. 5,195,53 to Sinko, et al., entitled "Infant Palate Protective Prosthesis" issued on Mar. 23, 1993.

In general, each of these prior art references discloses a method of making a custom-fitted device for use in the mouth of a premature infant. The base plate of each custom-made device has a surface which is particularly fitted to the palate of a particular infant by way of suction forces and dental powder. The base plate also has a longitudinally extending bore, along which the endotracheal tube is supported in a stabilized manner to prevent extubation. The custom-fitted base plate is made from rubber or soft plastic material designed to attenuate the constant pressure applied to the palate by the endotracheal tube during prolonged periods of intubation.

While the above described intraoral devices have reduced the possibility of groove formation associated with prolonged intubation using endotracheal tubes, such prior art devices and techniques suffer from a number of shortcomings and drawbacks.

In particular, prior art techniques for secure fixation of the endotracheal tube require the tight application of tape across the midface which, in turn, prevents the growth of this region resulting in maxillo facial hypoplasia.

Prior art devices require custom fitting and manufacture prior to use. This necessitates taking an impression of each infant's palate using a soft material in order to make a custom mold, and then making the device using the mold. This procedure often disturbs the infant, adds to the cost of using this tube stabilizing technique, and otherwise complicates matters in critical and intensive care units for neonatal care.

Often, the above-described prior art device fails to provide adequate protection to the alveolar ridge and lips of premature infants subject to prolonged intubation using endotracheal tubes. In addition, the custom fitted base plate is required to fit snugly to the infant's palate, creates a condition where bacteria can become entrapped and not easily removed without disrupting intubation. Thus by making it difficult to maintain oral hygiene, use of such prior art devices also increases the risk of oral infection.

Thus there is a great need in the art for an improved device for stabilizing endotracheal tubes and a method of using the same, without the accompanying shortcomings and drawbacks of prior art apparatus and methodologies.

OBJECTS OF THE PRESENT INVENTION

Accordingly, it is a primary object of the present invention to provide a system and method for stabilizing orotracheal tubes within the oral cavities of premature infants during prolonged intubation, while avoiding the shortcomings and drawbacks of prior art apparatus arid methodologies.

A further object of the present invention is to provide such a system and method for stabling orotracheal tubes within the oral cavities of premature infants during prolonged intubation, while effectively avoiding palatal groove formation and accidental extubation from premature infants and providing adequate protection to the alveolar ridge and lips and preventing midfacial hypoplasia.

A further object of the present invention is to provide such a system and method which does not require custom fitting of a base plate to each infant's palate in order to stably support orotracheal tubing within the oral cavities of particular infants.

A further object of the present invention is to provide such a system having intraoral and extraoral components of unitary construction that can be adjustably configured together for each particular infant prior to and during intubation.

A further object of the present invention is to provide such a system with a palate cushioning structure that is designed to loosely contact the palates of different infants without requiring custom fitting and molding procedures characteristic of prior art apparatus and methodologies.

A further object of the present invention is to provide such a system that minimizes pressure on the face and thus does not impair the growth of the mid face or cause maxillo facial hypoplasia.

A further object of the present invention is to provide such a system that prevents movement of the endotracheal tube into and out of the trachea as well as up and down within the trachea.

A further object of the present invention is to provide such a system, in which the palate cushioning structure is inflatable to adjust to different sizes.

A further object of the present invention is to provide such a system with a lip cushioning member that can be held in position by an elastic or like band, and an alveolar ridge cushioning flap portion that extends from the palate cushioning structure along its longitudinal axis.

A further object of the present invention is to provide such a system in which the lip cushioning flap portion is adjustably connected to the alveolar ridge cushioning flap portion while stably supporting a selected portion of the orotracheal tube disposed external to the infant's mouth during intubation.

A further object of the present invention is to provide such a system in which the palate cushioning structure is provided with a longitudinally extending more through which a portion of the orotracheal tube internal to the infant's mouth can be passed and supported securely therewithin, while an external portion of the orotracheal tube is supported by a support portion extending from the alveolar ridge cushioning flap portion.

A further object of the present invention is to provide such a system that is simply and inexpensive to manufacture, and which can be readily reconfigured to fit within the oral cavities of different infants.

These and further objects of the present invention will become apparent hereinafter.

SUMMARY OF THE INVENTION

In accordance with one aspect of the present invention, a system is provided for supporting endotracheal tubing in an infant during prolonged intubation. In general, the system comprises an intraoral component and an extraoral component, each of unitary construction. The intraoral components includes a base portion and an alveolar ridge cushioning flap portion. The base portion has a longitudinal extent, a bore formed along the longitudinal extent for passage and support of a first selected portion of the endotracheal tubing, and a palate facing surface made of a soft resilient material for cushioning the palate of the infant during fixation. The flexible alveolar ridge cushioning flap portion extends from the base portion substantially along the longitudinal extent thereof and has a generally smooth upper surface, a generally smooth lower surface, and a plurality of spaced apart projections extending from the generally smooth lower surface. The extraoral component of the system includes a flexible lip cushioning flap portion and a tubing clasping portion. The lip cushioning flap portion has a central portion, first and second end portions and a generally smooth lip contacting surface disposed between the first and second end portions. A centrally disposed hole is formed in the lip cushioning flap portion for releasable receipt of a selected one of the projections. A substantially rigid stem portion extends from the central portion of the lip cushioning flap portion. The tubing clasping portion extends from the substantially rigid stem portion, and is adapted to releasably clasp a second selected portion of the endotracheal tubing. In the illustrative embodiment, an elastic band or strap is connected to the first and second end portions of the lip cushioning flap portion in order to support the lip cushioning flap portion against the upper lip of the infant.

According to another aspect of the present invention, a method of using the endotracheal tubing support system is provided. According to the method, the first selected portion of the endotracheal tubing is passed through and supporting within the bore of the palate cushioning structure. The lip cushioning flap portion is supported against the upper lip of the infant by the elastic strap. The second selected portion of the endotracheal tubing is clasped by the tubing clasping portion. The upper surface of the flexible alveolar ridge cushioning flap portion is fitted snugly against the alveolar ridge of the infant, and a selected one or the projects is releasably retained in the centrally disposed hole in the lip cushioning flap portion. With this system configuration established, the intubing is stably supporting within the mouth of the infant while the palate is cushioned from the tubing by the palate facing surface and the alveolar ridge is cushioned from the tubing by the upper surface of the flexible alveolar ridge cushioning flap portion.

Numerous advantages provided by the present invention will become apparent hereinafter.

BRIEF DESCRIPTION OF THE DRAWINGS

For a more complete understanding of the Objects of the Present Invention, the Detailed Description of the Illustrative Embodiment of the Present Invention is to be read in connection with the following drawings, in which.

DETAILED DESCRIPTION OF THE ILLUSTRATIVE EMBODIMENT

Figure 1:
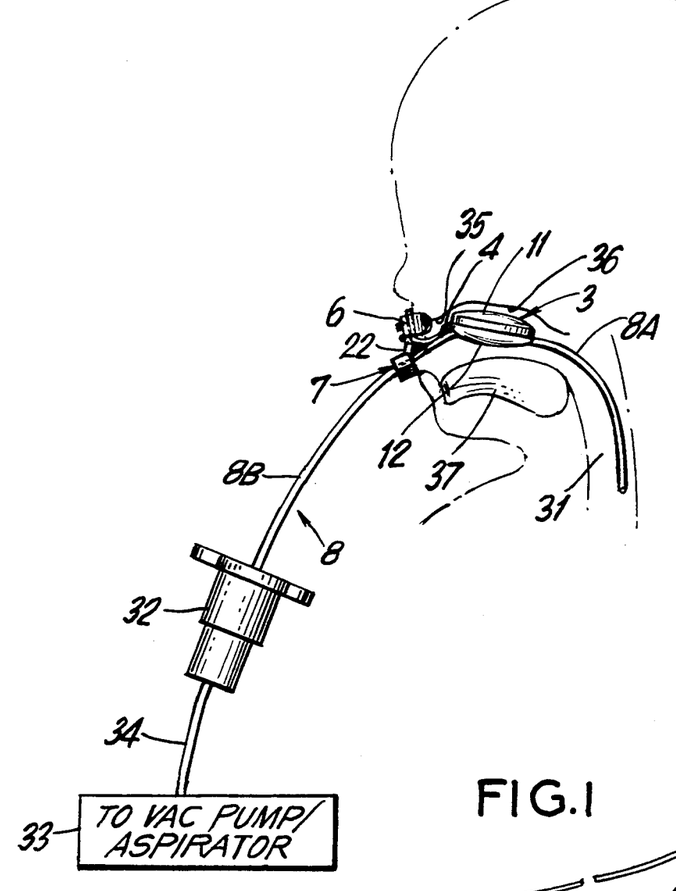
FIG. 1 is a perspective view of the endotracheal tube supporting system of the first illustrative embodiment of the present invention, shown assembled in a first adjusted configuration and installed within the mouth of a schematically illustrated infant.
Figure 2:
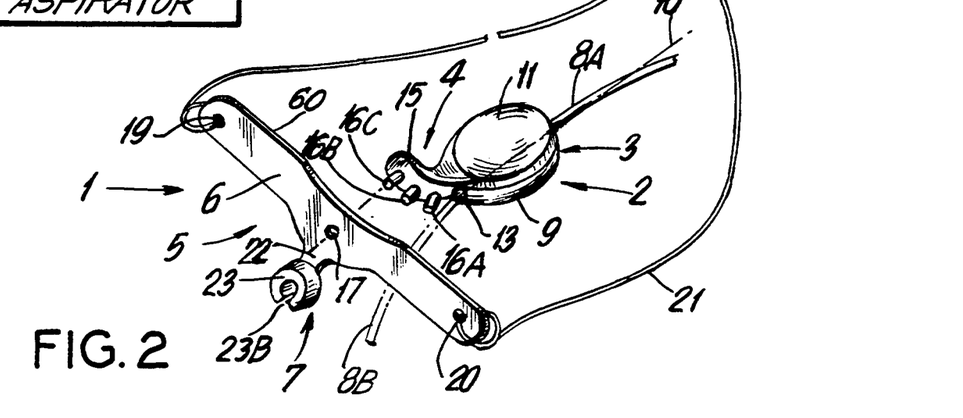
FIG. 2 is a perspective view illustrating the method of configurating the intraoral and extraoral system components of the present invention.

As illustrated in FIG. 1 and 2 in particular, the endotracheal tube supporting system 1 of the first illustrative embodiment of the present invention comprises two separate, yet reconfigurable components, namely: an intraoral components 2 including a palate cushioning structure 3 and an alveolar ridge cushioning flap portion 4 extending therefrom; and an extraoral component 5 including flexible upper lip cushioning flap 6 and a tube clasping portion 7. As will be described hereinafter, these components are designed to be configured together, along with a length of endotracheal tube or tubing 8, so as to provide an adjustable system that can be easily used to support and stabilize the endotracheal tubing during prolonged intubation of infants, without the risk of complications associated with prior art apparatus and methodologies.

Figures 3, 6:
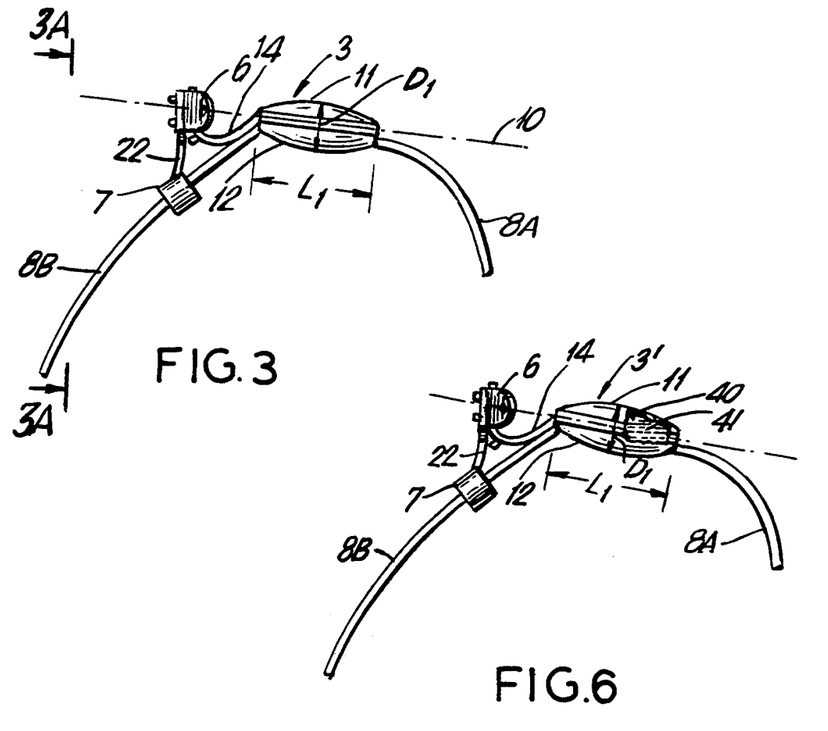
FIG. 3 is a perspective view of the system of the present invention, shown removed from the mouth of the premature infant, and assembled together and connected to orotracheal tubing.
FIG. 6 is a perspective view of a second illustrative embodiment of the endotracheal tube supporting system of the present invention, showing the arrangement of an inflated bladder within the palate cushioning structure of intraoral component thereof.

As shown in FIGS. 1, 2, and 3, palate cushioning structure 3 of the first illustrative embodiment has a base portion 9 of tablet-shaped geometry, with a longitudinal extent defined along longitudinal axis 10. Palate cushioning structure 3 also has an easily deformable palate facing surface 11, a more rigid tongue facing surface 12, and a cylindrical bore 13 formed along longitudinal axis 10. Preferably, the maximal distance $D_1$ between the palate facing surface and the tongue facing surface is selected to be in the range from about 5.2 to about 10.2 millimeters. The cross-sectional diameter of cylindrical bore 13 is selected to permit slidable passage of conventional endotracheal tubing, whereas the length of the bore $L_1$ is commensurate with the length of the palate over which the orotracheal tubing would normally contact, but for the presence of the palate cushioning structure. Preferably, the bore length is selected to be in the range of from about 10.0 to about 22.2 millimeters. The function of cylindrical bore 13 is to permit passage of endotracheal tubing section 8A through base portion 9, to securely hold the tubing within the base portion, while allowing palate facing surface 11 to resiliently attenuate those forces directed towards the palate by tubing section 8A during intubation.

As best shown in FIGS. 2 and 3 when in its relaxed (non-configured) state, alveolar ridge cushioning flap portion 4 extends from base portion 3 of the palate cushioning structure, and along longitudinal axis. Alveolar ridge cushioning flap portion 3 has a generally smooth upper surface 14 and a generally smooth lower surface 15. Preferably, the alveolar ridge cushioning flap portion has a length in the range from about 14.5 to about 22.0 millimeters, and a width in the range from about 9 to about 15 millimeters.

As best shown in FIG. 2, a plurality of flexible, spaced apart projections (i.e., buttons) 16A, 16B, 16C extend from the lower surface of the alveolar ridge cushioning flap portion. Each projection has a cylindrical geometry and extends perpendicularly from lower surface 15 of the alveolar ridge cushioning flap portion.

Preferably, the height of each of these projections is about 4.0 millimeters, which is slightly greater than the thickness of the lip cushioning flap portion and the lip cushioning flap portion. To prevent facial distortion, the physical characteristics of the alveolar ridge cushioning flap portion are softness and flexibility. To protect the palate from forces exerted by the endotracheal tubing passed through bore 10 in the base portion, the physical characteristics of the palate facing surface 11 are softness and resiliency. Significantly, snug molding of palate facing surface 11 to the palate need not necessarily occur, and in accordance with the principles of the present invention, does not occur during the use of the system hereof. Advantageously, this feature of the present invention minimizes the risk of infection.

As shown, the alveolar ridge cushioning flap portion and the palate cushioning structure are co-molded together to provide an intraoral component of unitary construction. It is believed that a number of different types of suitable material may be used to make the intraoral component while satisfying the design characteristics set forth above. In the preferred embodiment, the palate facing surface 11 is made from a rubber material such as suitable silicone elastomer having a hardness specified by a durometric reading of 30 (−15, +0) on the Shore A scale (i.e., 30 Shore A), The tongue facing surface 12 and alveolar ridge cushioning strap portion 4 are each formed from like material having a hardness of 55 Shore A. Rubber material having such durometric properties is made by mixing silicone elastomer (i.e., the base ingredient) with clays, oils and natural latex rubber in a manner known in the art. Preferably, liquid chlorine is used as a vulcanizing agent. Suitable manufacturing techniques for this system component include injection co-molding processes well known in the art.

Figure 3A:
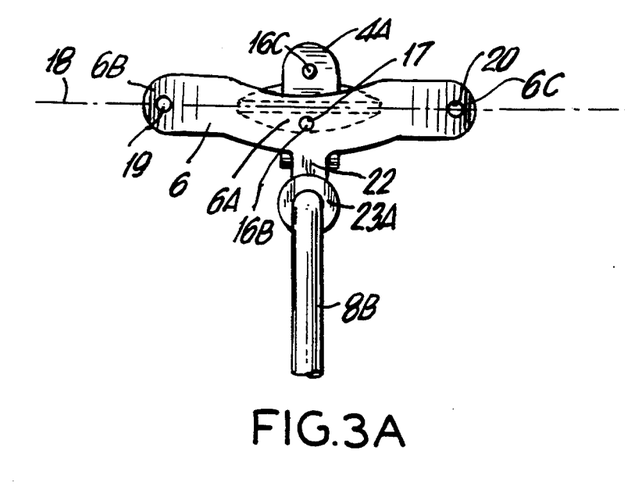
FIG. 3A is an elevated end view of the system of the present invention, taken along line 3A—3A of FIG. 3.
Figure 4:
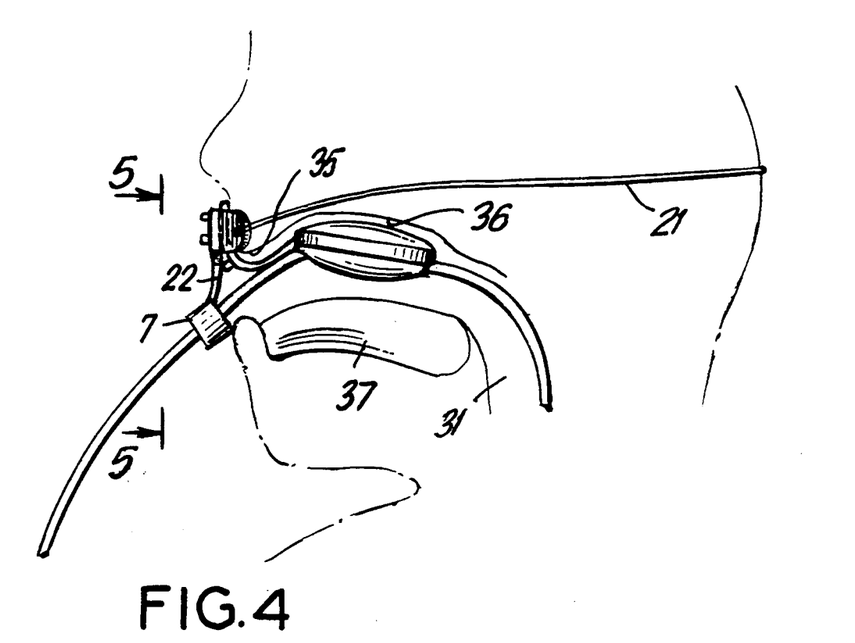
FIG. 4 is an perspective view of the endotracheal tubing supporting system of the first illustrative embodiment of the present invention, shown assembled in a second adjusted configuration and installed within the mouth of a schematically illustrated infant.
Figure 5:
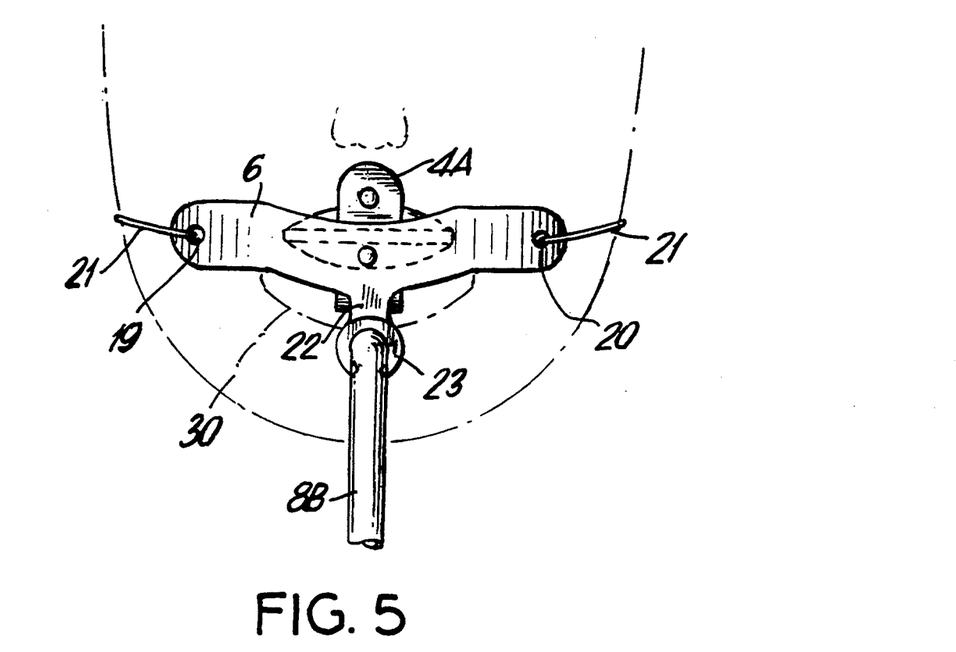
FIG. 5 is an elevated view of the endotracheal tube supporting system of the first illustrative embodiment of the present invention taken along line 5—5 of FIG. 4.

As best shown in FIGS. 2 and 3A, flexible lip cushioning flap portion 6 has a number of primary structural features, namely: a longitudinal extent along a longitudinal axis 18; a central portion 6A, and first and second end portions 6B and 6C; a generally smooth lip contacting (i.e., rear) and surface 6D; a generally smooth front surface 6E; projection receiving (i.e., button) hole 17 formed through central portion 6A; and a pair of holes 19 and 20 formed in first and second end portions 6B and 6C. As shown in FIG. 4, the function of projection receiving hole 17 is to releasably receive (i.e., engage) a selected one of the plurality of projections 16A, 16B, 16C when the alveolar ridge cushioning flap portion is fitted snugly against the surface contour of the alveolar ridge of the infant. As shown in FIG. 5, the function of holes 19 and 20 is to facilitate fastening of the opposing ends of an elastic cord 21 or like structure. With such an arrangement, the elastic cord 21 can encircle the back of the infant's head and thereby safely supports the lip cushioning flap portion 6 gently against the upper lip and cheeks of the infant during intubation.

As best shown in FIGS. 2 and 3A, rigid stem portion 22 extends orthogonally from the longitudinally axis of the flexible lip cushioning flap portion and terminates in tube clasping portion 23. As shown, tube clasping portion 23 comprises a flexible annular-shaped clasp 23A having a cutout 23B aligned along the longitudinal extent of the stem portion, and a circular aperture 23C particularly adapted to releasably clasp a selected portion of orotracheal tubing section 8B disposed external to an infant's mouth. Unlike the lip cushioning and alveolar ridge cushioning flap portions, the stem and tube clasping portions have rigid physical characteristics, as the function of these structures is to stably supporting tubing 8 between the upper and lower lips of the infant during intubation, as shown in FIGS. 1, 4 and 5 in particular. In the preferred embodiment, lip cushioning flap portion is formed by co-molding a rubber material having about 55 Shore A hardness (±15 points), while the tube clasping portion is formed by co-molding rubber material having about 90 Shore A hardness (+10, −0 points). During the same co-molding process, the stem portion is formed from rubber material having about an 80 Shore A hardness (±10 points). Notably, the 80-Shore A hardness of the stem portion results from the intermixing of the 55 Shore A rubber material with the 90 Shore A rubber material during the co-molding injection process.

In some applications, it might be desired to manufacture the intraoral and extraoral system components in various sizes for premature infants, and to stock the same in the critical care units of hospitals for selection and use as required for particular infants. Notwithstanding such possible applications, a preferred length dimension for the alveolar ridge cushioning portion is in the range of about 14.5 to about 22.0 millimeters, while a preferred length dimension therefor is in the range of from about 9 to about 15 millimeters. Exemplary length and width dimensions for the lip cushioning flap portions are about 19.0 and 9.0 millimeters, respectively. Typically, the combined mass of the intraoral and extraoral components of the system, less the mass of endotracheal tubing, will be in the range from about 2.0 to about 6.0 milligrams, thus further minimizing the possibility of facial or other distortion due to gravitational loading. It is understood, however, that such physical dimensions and mass specifications may and typically will vary from one embodiment of the present invention to another embodiment thereof.

Having described the structural and functional features of the system of the present invention, it is appropriate at this junction to describe a preferred method of using the system in premature infants.

The first step of the method involves selecting a suitable length of endotracheal tubing and sliding one end thereof through the cylindrical bore formed in the intraoral component 2. After the intraoral component is positioned on the tubing, at about 9.0 centimeters from the distal end thereof, the distal end is introduced through the mouth 30 of the infant and into his or her tracheal 31 in a conventional manner. Then, as shown in FIG. 1, the proximal end of the tubing length that terminates in a conventional connector 32 is connected to a mechanical ventilator 33 or like machine using another section of tubing 34 and in a manner well known in the art. Then as shown in FIG. 2, the opposing ends of an elastic band or strap 21 are connected to holes 19 and 20 in the lip cushioning flap portion. Then, as shown in FIG. 4, the lip cushioning flap portion is placed against the upper lip of the infant, and the elastic band is placed behind the back of the infant's head in order to hold the lip cushioning flap portion in place on the infant. The alveolar ridge cushioning flap, portion is then adjusted to fit over and protect the infant's alveolar ridge 35, and the end portion thereof 4A is manually pulled up between the upper lip of the infant and the central portion of the lip cushioning flap so that excess slack is taken up and snug fit is attained. In this system configuration, the projection 16A, 16B or 16C which is closest to central hole 17 in the lip cushioning flap portion, is manually pushed through the central hole and secured therewithin to join the intraoral and extraoral components of the system.

In a properly adjusted system configuration as shown in FIGS. 1 and 4, the alveolar lip cushioning flap portion fits snugly against and substantially conforms to the general contour of the alveolar ridge thereby protecting it against the accidental trauma occasioned during intubation. At the same time, palate facing surface 11 of the palate cushioning structure is loosely positioned against the palate 36, thereby permitting fluid, such oral rinse, to flow therebetween during oral hygiene procedures performed upon the infant during intubation. Because of the low profile characteristics of the base portion 3, the infant's tongue 37 is permitted to contact the smooth surface thereof 12 with minimal obstruction. Notably, unlike prior art techniques, the use of dental powder or like adhesives are not utilized in practicing the method of the present invention. If it is determined that a more snug fit is desired or required between the alveolar ridge cushioning flap and the infant's alveolar ridge, all that the doctor or nurse need do is un-snap (i.e., unbutton) the alveolar ridge cushioning flap, manually pull the end portion 4A thereof upwards (like a tongue on a shoe), and then snap the next projection 16B or 16A through central hole 17 in the lip cushioning flap portion.

In an alternative embodiment of the system of the present invention, the palate cushioning structure of the intraoral component can be designed as an inflatable structure of table-shaped geometry. As shown in FIG. 6, the interior of the inflatable palate cushioning structure $3^1$ has all of the structural characteristics of the embodiment shown in FIGS. 1–5, with the following structural modifications. In particular, rather than having a solid upper interior portion between the palate facing surface 11 and bone 13, a hollow deformable chamber 40 is provided therebetween. As illustrated in FIG. 6, air, liquid, or other compressible fluid 41 is contained within hollow chamber 40 in order to provide palate facing surface 11 with deformable surface characteristics. This allows the palate facing surface to easily and comfortably adapt to the surface contour of any particular individual infant, while damping forces exerted towards the palate by endotracheal tubing 8.

The illustrative embodiments of the present invention has been disclosed in connection with orotracheal type ET tubes. However, the present invention can also be used with nasotracheal tubes as well. In such cases, a section of nasotracheal tubing is placed through the nasal passageway of the patient and into his or her trachea. Then, only the extraoral clasp portion of the system is used to hold the endotracheal tube in place.

Also, the system of the present invention may be used in any pediatric patient and is not restricted to neonatals. In older patients, only the extraoral component of the system need be used.

In an alternative embodiment of the present invention, the palate cushioning structure of the intraoral component can be designed as an inflatable structure of table-shaped geometry. As shown in FIG. 6, the interior of the inflatable palate cushioning structure $3^1$ has all of the structural characteristics of the embodiment shown in FIGS. 1–5, with the following structural modifications. In particular, rather than having a solid upper interior portion between the palate facing surface 11 and bone 13, a hollow deformable chamber 40 is provided therebetween. As illustrated in FIG. 6, air, liquid, or other compressible fluid 41 is contained within hollow chamber 40 in order to provide palate facing surface 11 with deformable surface characteristics. This allows the palate facing surface to adapt to the surface contour of any particular individual infant.

While the illustrative embodiment of the present invention will be useful in many intubation applications, various modifications to the present invention will readily occur to persons with ordinary skill in the art. All such modifications and variations are deemed to be within the scope and spirit of the present invention as defined by the appended claims to invention.

What is claimed is:

1. A system for supporting an endotracheal tube in the trachea of pediatric patient, comprising:
   (a) an intraoral component of unitary construction including
      a base portion having a longitudinal extent, a bore formed along said longitudinal extent for passage and support of a first selected portion of an endotracheal tube, and a facing surface made of a soft resilient material for cushioning the palate of the patient during intubation, and
      a flexible alveolar ridge cushioning flap portion extending from said base portion substantially along the longitudinal extent of said base portion, and having a generally smooth upper surface, a generally smooth lower surface and a plurality of spaced apart projections extending from said generally smooth lower surface; and
   (b) an extraoral component of unitary construction including
      a flexible lip cushioning flap portion having a central portion, first and second end portions and a generally smooth lip contacting surface between said first and second end portions,
      a centrally disposed hole for releasable receipt of a selected one of said projections,
      a substantially rigid stem portion extending from said central portion,
      a tube clasping portion extending from said substantially rigid stem portion, for releasably clasping a second selected portion of an endotracheal tube, and
      supporting means, operably connected to said first and second end portions, for supporting said lip cushioning flap portion against the upper lip of the patient.

2. The system of claim 1 further comprising an endotracheal tube having first and second selected portions, wherein
   (a) the first selected portion of the endotracheal tube is passed through and supported within said bore,
   (b) said lip cushioning flap portion is supported against the upper lip of the infant by said supporting means,
   (c) the second selected portion of said endotracheal tube is clasped by said tube clasping portion,
   (d) the upper surface of said flexible alveolar ridge cushioning flap portion is fitted snugly against the alveolar ridge of the patient, and
   (e) a selected one of said projections is releasably retained in said centrally disposed hole, then the endotracheal tube is stably supported within the mouth of the patient while the palate is cushioned from said tubing by said palate facing surface and the alveolar ridge is cushioned from said endotracheal tube by the upper surface of said flexible alveolar ridge cushioning flap portion.

3. The system of claim 1, wherein said intraoral and extraoral components are made from a plastic material.

4. The system of claim 3, wherein said plastic material includes elastomeric silicone.

5. The system of claim 1, wherein said alveolar ridge cushioning flap portion has a length in the range from about 14.5 to about 22.0 millimeters, and a width in the range from about 9 to about 15 millimeters.

6. The system of claim 1, wherein the total mass of said intraoral and said extraoral components is in the range from about 2.0 to about 6.0 millimeters.

7. The system of claim 1, wherein said supporting means comprises an elastic adapted to connect to the first and second end portions of said lip cushioning flap portion and encircle the cheeks and head of the infant.

8. The system of claim 1, wherein the spacing of each said projection is in the range from about 3.5 to about 4.0 millimeters.

9. The system of claim 1, wherein the length of said cylindrical bore is in the range from about 10.0 to about 22.0 millimeters.

10. The system of claim 1, wherein the maximal thickness between said palate facing surface and said tongue facing surface is less than about 10.2 millimeters.

11. A method of supporting a section of an endotracheal tube in the mouth and trachea of pediatric patient, comprising the steps:
    (a) providing a system including an endotracheal tube an intraoral component and an extraoral component, each of unitary construction, said intraoral component including
       a base portion having a longitudinal extent, a bore formed along said longitudinal extent for passage and support for a first selected portion of said endotracheal tube, and a palate facing surface made of a soft resilient material for cushioning the palate of the patient during intubation, and
    a flexible alveolar ridge cushioning flap portion extending from said base portion substantially along the longitudinal extent of said base portion, and having a generally smooth upper surface, a generally smooth lower surface and a plurality of spaced apart projections extending from said generally smooth lower surface, and said extraoral component including
       a flexible lip cushioning flap portion having a central portion, first and second end portions and a generally smooth lip contacting surface between said first and second end portions,
       a centrally disposed hole for releasable receipt of a selected one of said projections,
       a substantially rigid stem portion extending from said central portion,
       a tube clasping portion extending from said substantially rigid stem portion, for releasably clasping a second selected portion of said endotracheal tube, and
       supporting means, operably connected to said first and second end portions, for supporting said lip cushioning flap portion against the upper lip of the patient;
    (b) passing the first selected portion of said endotracheal tube through said bore so as to support said first selected portion therein;
    (c) supporting said lip cushioning flap portion against the upper lip of the infant using said supporting means;

(d) clasping the second selected portion of said section of said endotracheal tube within said tube clasping portion;
(e) fitting the upper surface of said flexible alveolar ridge cushioning flap portion snugly against the alveolar ridge of the patient; and
(f) releasably retaining a selected one of said projections in said centrally disposed hole,
   whereby said first selected portion of endotracheal tube is stably supported within the mouth of the patient while the palate is cushioned from the second selected portion of said endotracheal tube by said palate facing surface, and the alveolar ridge is cushioned from said first and second selected portions of said endotracheal tube by the upper surface of said flexible alveolar ridgy cushioning flap portion.

12. The method of claim 11, providing intraoral and extraoral components which are made from a plastic material selected from the group consisting of elastic.

13. The method of claim 11, providing an alveolar ridge cushioning flap portion which has a length in the range from about 14.5 to about 22.0 millimeters, and a width in the range from about 9.0 to about 15.0 millimeters.

14. The method of claim 11, providing a total mass of said intraoral and said extraoral components in the range from about 2.0 to about 6.0 milligrams.

15. The method of claim 11, providing a supporting means comprises an elastic element adapted to connect to the first and second end portions of said lip cushioning flap portion and encircle the cheeks and head of the patient.

16. The method of claim 11, spacing apart each of said projections in the range from about 3.5 to about 4.0 millimeters.

17. The method of claim 11, providing a length of said cylindrical bore is in the range from about 10.0 to about 22.0 millimeters.

18. The method of claim 11, providing a maximal thickness between said palate facing surface and said tongue facing surface which is less than about 10.2 millimeters.

* * * * *